(12) United States Patent
Riederer

(10) Patent No.: US 8,918,159 B2
(45) Date of Patent: Dec. 23, 2014

(54) SYSTEM AND METHOD FOR IMPROVED ACCELERATED MAGNETIC RESONANCE IMAGING USING ROI MASKING

(75) Inventor: Stephen J Riederer, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 465 days.

(21) Appl. No.: 13/449,500

(22) Filed: Apr. 18, 2012

(65) Prior Publication Data

US 2013/0281831 A1   Oct. 24, 2013

(51) Int. Cl.
*A61B 5/055* (2006.01)

(52) U.S. Cl.
USPC .......................................... 600/410; 600/420

(58) Field of Classification Search
USPC ................................. 600/410, 420
See application file for complete search history.

(56) References Cited

U.S. PATENT DOCUMENTS

| 6,841,998 B1 | 1/2005 | Griswold |
| 7,760,939 B2 | 7/2010 | Zwanger |

OTHER PUBLICATIONS

Earls, et al., Hepatic Arterial-Phase Dynamic Gadolinium-Enhanced MR Imaging: Optimization with a Test Examination and a Power Injector, Radiology, 1997, 202:268-273.
Griswold, et al., Generalized Autocalibrating Partially Parallel Acquisitions (GRAPPA), Magnetic Resonance in Medicine, 2002, 47:1202-1210.
Haider, et al., 3D High Temporal and Spatial Resolution Contrast-Enhanced MR Angiography of the Whole Brain, Magnetic Resonance in Medicine, 2008, 60(3):749-760.
Haider, et al., Peripheral Vasculature: High-Temporal- and High-Spatial-Resolution Three-Dimensional Contrast-Enhanced MR Angiography, Radiology, 2009, 253(3):831-843.
Koktzoglou, et al., Highly Accelerated Contrast-Enhanced MR Angiography: Improved Reconstruction Accuracy and Reduced Noise Amplification With Complex Subtraction, Magnetic Resonance in Medicine, 2010, 64:1843-1848.
Mostardi, et al., Contrast-Enhanced MR Angiography of the Abdomen with Highly Accelerated Acquisition Techniques, Radiology, 2011, 261:587-597.
Pruessmann, et al., SENSE: Sensitivity Encoding for Fast MRI, Magnetic Resonance in Medicine, 1999, 42:952-962.
Weiger, et al., 2D SENSE for Faster 3D MRI, Magnetic Resonance Materials in Physics, Biology and Medicine, 2002, 14(1):10-19.
Wilman, et al., Fluoroscopically Triggered Contrast-Enhanced Three-Dimensional MR Angiography with Elliptical Centric View Order: Application to the Renal Arteries, Radiology, 1997, 205:137-146.
Wilman, et al., Performance of an Elliptical Centric View Order for Signal Enhancement and Motion Artifact Suppression in Breath-Hold Three-Dimensional Gradient Echo Imaging, Magnetic Resonance in Medicine, 1997, 38 (5):793-802.
Wu et al., Improved Matrix Inversion in Image Plane Parallel MRI, Magnetic Resonance Imaging, 2009, 27:942-953.

*Primary Examiner* — Peter Luong
(74) *Attorney, Agent, or Firm* — Quarles & Brady, LLP

(57) ABSTRACT

A system and method for creating at least one angiographic image using a magnetic resonance imaging (MRI) system includes acquiring, with the MRI system and using parallel imaging techniques, a pre-contrast image data set and a post-contrast image data set of a portion of a subject having a vascular structure extending therethrough and subtracting the pre-contrast and the post-contrast image data set to generate a difference angiogram data set. The method includes reconstructing the difference angiogram data set into at least one aliased angiogram, creating a region of interest (ROI) mask from an image of the portion of the subject, and indicating a masking border surrounding the vascular structure and substantially excluding tissues surrounding the vascular structure. The method then includes de-aliasing the at least one aliased angiogram using the ROI mask to create an angiogram of the portion of the subject.

20 Claims, 6 Drawing Sheets

SYSTEM AND METHOD FOR IMPROVED ACCELERATED MAGNETIC RESONANCE IMAGING USING ROI MASKING

STATEMENT REGARDING FEDERALLY SPONSORED RESEARCH

This invention was made with government support under HL070620 awarded by the National Institutes of Health. The government has certain rights in this invention.

BACKGROUND OF THE INVENTION

The present invention relates generally to magnetic resonance imaging ("MRI") systems and methods and, more particularly, the invention relates to systems and methods for producing images using parallel imaging using specialized masking techniques tailored to regions of interest within the subject of the parallel imaging study.

Magnetic resonance imaging ("MRI") uses the nuclear magnetic resonance ("NMR") phenomenon to produce images. When a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped," into the x-y plane to produce a net transverse magnetic moment $M_{xy}$. A signal is emitted by the excited nuclei or "spins," after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically-proven pulse sequences and they also enable the development of new pulse sequences.

The MR signals acquired with an MRI system are signal samples of the subject of the examination in Fourier space, or what is often referred to in the art as "k-space." Each MR measurement cycle, or pulse sequence, typically samples a portion of k-space along a sampling trajectory characteristic of that pulse sequence. Most pulse sequences sample k-space in a raster scan-like pattern sometimes referred to as a "spin-warp," a "Fourier," a "rectilinear," or a "Cartesian" scan. The spin-warp scan technique employs a variable amplitude phase encoding magnetic field gradient pulse prior to the acquisition of MR spin-echo signals to phase encode spatial information in the direction of this gradient. In a two-dimensional implementation ("2DFT"), for example, spatial information is encoded in one direction by applying a phase encoding gradient, $G_y$, along that direction, and then a spin-echo signal is acquired in the presence of a readout magnetic field gradient, $G_x$, in a direction orthogonal to the phase encoding direction. The readout gradient present during the spin-echo acquisition encodes spatial information in the orthogonal direction.

In a typical 2DFT pulse sequence, the magnitude of the phase encoding gradient pulse, $G_y$, is incremented, $\Delta G_y$, in the sequence of measurement cycles, or "views" that are acquired during the scan to produce a set of k-space MR data from which an entire image can be reconstructed.

Magnetic resonance angiography (MRA) uses the magnetic resonance phenomenon to produce images of the human vasculature. To enhance the diagnostic capability of MRA a contrast agent such as gadolinium can be injected into the patient prior to the MRA scan. When using a contrast agent, such vascular imaging is typically referred to a contrast enhanced MRA (CE-MRA or CEMRA). In practice, a moderate amount (10-30 ml) of a gadolinium-based contrast agent is typically injected into an arm vein. The contrast material then mixes with the systemic blood in the heart and pulmonary vasculature and passes from the left heart into the arterial circulation. The presence of contrast material in the blood causes the net T1 relaxation time to be altered from its unenhanced value, for example, of about 1000 msec to values in the range, for example, of 50 to 100 msec. MR acquisition methods can exploit this change in T1, causing the enhanced blood within the vasculature to be significantly brighter compared to other structures within the imaging FOV.

There are a wide variety of technical challenges to performing CE-MRA to yield the desired information for a particular setting. As described in U.S. Pat. No. 5,417,213 the trick with this CE-MRA method is to acquire the central k-space views at the moment the bolus of contrast agent is flowing through the vasculature of interest. Collection of the central lines of k-space during peak arterial enhancement is key to the success of a CE-MRA exam. If the central lines of k-space are acquired prior to the arrival of contrast, severe image artifacts can limit the diagnostic information in the image. Alternatively, arterial images acquired after the passage of the peak arterial contrast are sometimes obscured by the enhancement of veins. In many anatomic regions, such as the carotid or renal arteries, the separation between arterial and venous enhancement can be as short as 6 seconds. However, this timing constraint is in opposition with the need to obtain a high spatial resolution image, for example, a three-dimensional (3D) image with adequate spatial resolution. To do so, it is necessary to have a sufficiently long acquisition time, generally in the range of ten seconds or longer, in order to collect enough information to yield the desired spatial resolution The short separation time between arterial and venous enhancement dictates the use of acquisition sequences of either low spatial resolution or very short repetition times (TR). Short TR acquisition sequences severely limit the signal-to-noise ratio (SNR) of the acquired images relative to those exams in which longer TRs are possible. The rapid acquisitions required by first-pass CE-MRA methods thus impose an upper limit on either spatial or temporal resolution.

As a result, depending on the technique used and the trade-offs that may be tolerated in a given clinical setting, it may be possible to utilize one of a variety of different strategies that have been developed to shorten the scan time. For example, one such strategy is referred to generally as "parallel MRI" ("pMRI"). Parallel MRI techniques use spatial information from arrays of radio frequency ("RF") receiver coils to substitute for the spatial encoding that would otherwise have to be obtained in a sequential fashion using RF pulses and magnetic field gradients, such as phase and frequency encoding gradients. Each of the spatially independent receiver coils of the array carries certain spatial information and has a different spatial sensitivity profile. This information is utilized in order to achieve a complete spatial encoding of the received MR signals, for example, by combining the simultaneously acquired data received from each of the separate coils.

Parallel MRI techniques allow an undersampling of k-space by reducing the number of acquired phase-encoded k-space sampling lines, while keeping the maximal extent covered in k-space fixed. The combination of the separate MR signals produced by the separate receiver coils enables a reduction of the acquisition time required for an image, in comparison to a conventional k-space data acquisition, by a factor generally bounded by the number of the receiver coils. Thus, the use of multiple receiver coils acts to multiply imaging speed, without increasing gradient switching rates or RF power.

Two categories of such parallel imaging techniques that have been developed and applied to in vivo imaging are so-called "image space methods" and "k-space methods." An exemplary image space method is known in the art as sensitivity encoding ("SENSE"), while an exemplary k-space method is known in the art as simultaneous acquisition of spatial harmonics ("SMASH"). With SENSE, the undersampled k-space data is first Fourier transformed to produce an aliased image from each coil, and then the aliased image signals are unfolded by a linear transformation of the superimposed pixel values. With SMASH, the omitted k-space lines are synthesized or reconstructed prior to Fourier transformation, by constructing a weighted combination of neighboring k-space lines acquired by the different receiver coils. SMASH requires that the spatial sensitivity of the coils be determined, and one way to do so is by "autocalibration" that entails the use of variable density k-space sampling. A more recent advance to SMASH techniques using autocalibration is a technique known as generalized autocalibrating partially parallel acquisitions ("GRAPPA"), as described, for example, in U.S. Pat. No. 6,841,998. With GRAPPA, k-space lines near the center of k-space are sampled at the Nyquist frequency, in comparison to the undersampling employed in the peripheral regions of k-space. These center k-space lines are referred to as the so-called autocalibration signal ("ACS") lines, which are used to determine the weighting factors that are utilized to synthesize, or reconstruct, the missing k-space lines.

When applied to CE-MRA acquisitions, short repetition time (TR) gradient echo sequences allow rapid collection of MRI data, and this can be accelerated with undersampling techniques such as SENSE and GRAPPA. Synchronizing the acquisition to the contrast arrival can be done using a test bolus or fluoroscopic triggering, such as described by Wilman A H, Riederer S J, King B F, Debbins J P, Rossman P J, Ehman R L. Fluoroscopically-triggered contrast-enhanced three-dimensional MR angiography with elliptical centric view order: application to the renal arteries. Radiology 1997; 205: 137-146. An extension of the acquisition duration well into the venous phase, but with negligible venous signal, can be done using various centric phase encoding view orders, such as described by Wilman A H, Riederer S J. Performance of an elliptical centric view order for signal enhancement and motion artifact suppression in breathhold three dimensional gradient echo imaging. Magn Reson Med 1997; 38:793-802.

CE-MRA has been used successfully to image many vascular regions of the body, such as the intracranial, carotid, and renal arteries and the arteries of the peripheral vasculature. In particular, SENSE acceleration with typical acceleration applied along the two phase encoding directions has been useful in driving down the acquisition times in the brain, periphery, and abdomen, with 2D acceleration factors (R) as high as R=8. However, at this level of acceleration, the degree of loss of signal-to-noise ratio (SNR) due to the extensive level of undersampling, and the accompanying high level of aliasing, can become problematic.

It is well known that knowledge regarding an object that lies within the field of view (FOV) and what regions within the FOV might not contain any object can be used with traditional SENSE acquisitions to provide improved performance and temper the SNR loss. Such processes typically employ or are referred to "masking" techniques. Though particular masking techniques may vary slightly, masking techniques typically involve an attempt to determine the edges or borders of the object being imaged. Using these determined edges or borders, voxels falling outside of the borders are assumed to have no magnetization, and thus no MRI signal. Specifically, during the SENSE inversion process, these voxels are forced to have zero signal, which causes the algebraic inversion of the SENSE equations involving those zeroed voxels to be simplified, eliminates the spurious dispersion of signal to those voxels, and more properly assigns the measured signal to voxels actually located within the object.

Of course, the clinical suitability of such masking techniques is directly correlated to the accuracy of the determined edges or borders. However, the accuracy of the determined edges or borders is typically dependent upon the amount of time and information available to the clinician in making the determination. For example, highly accurate edges or borders could be determined by a clinician by acquiring a high-accurate anatomical image of the subject as a precursor to the SENSE-based acquisition. However, such an additional imaging acquisition would typically substantially extend the duration of the overall imaging process and, in some cases, defeat the purpose of attempting to accelerate the imaging process using SENSE.

It would therefore be desirable to provide a system and method for performing contrast enhanced MRA imaging studied employing parallel imaging without suffering clinically-unacceptable loss of SNR or a high level of aliasing, but without requiring clinicians to perform extensive pre-planning or additional imaging acquisitions that undermine the improvements in throughput that parallel imaging is typically selected to provide.

SUMMARY OF THE INVENTION

The present invention overcomes the aforementioned drawbacks by providing a system and method for performing parallel imaging using masking in standard SENSE acceleration techniques that is adapted to specific situations encountered in contrast-enhanced MRA in which difference images are formed of the vasculature pre- and post-contrast. The present invention recognizes that in properly-performed CE-MRA difference imaging acquisitions, contrast-filled vessel lumens typically comprise a very small percentage of the voxels within the object, such as only approximately 10 percent or less. Thus, the present invention recognizes that typically 90 percent or more of the voxels within the FOV can be masked out of the SENSE reconstruction process because they are not contained within the vessel lumen. This recognition provides markedly improved performance compared to the 20 percent to 30 percent that are masked because they are not within the object. Thus, the present invention provides improved performance because it enables substantially more voxels to be masked from the SENSE reconstruction, specifically those that are within the object but known to not lie within the vascular structures of interest, than is possible with traditional SENSE CE-MRA techniques employing masks.

In accordance with one aspect of the invention, a method of creating at least one angiographic image using a magnetic resonance imaging (MRI) system is disclosed that includes acquiring, with the MRI system and using parallel imaging techniques, a pre-contrast image data set and a post-contrast image data set of a portion of a subject having a vascular structure extending therethrough. The method also includes subtracting the pre-contrast image data set and the post-contrast image data set to generate a difference angiogram data set and reconstructing the difference angiogram data set into at least one aliased angiogram. The method further includes creating a region of interest (ROI) mask from an image of the portion of the subject including the vascular structure and indicating a masking border surrounding the vascular structure and substantially excluding tissues surrounding the vascular structure. The method then includes de-aliasing the at least one aliased angiogram using the ROI mask to create an angiogram of the portion of the subject.

In accordance with another aspect of the invention, a magnetic resonance imaging (MRI) system is disclosed that includes a magnet system configured to generate a polarizing magnetic field about at least a portion of a subject arranged in the MRI system and a plurality of gradient coils configured to apply a gradient field to the polarizing magnetic field. The system also includes a radio frequency (RF) system configured to apply an excitation field to the subject and acquire MR image data therefrom in parallel from a plurality of channels and a computer system. The computer system is programmed to at least carry out the steps of acquiring a pre-contrast image data set and a post-contrast image data set of a portion of a subject having a vascular structure extending therethrough and subtracting the pre-contrast image data set and the post-contrast image data set to generate a difference angiogram data set. The computer is further programmed to carry out the steps of reconstructing the difference angiogram data set into at least one aliased angiogram and creating a region of interest (ROI) mask indicating a masking border surrounding the vascular structure and substantially excluding tissues surrounding the vascular structure. The computer is also programmed to carry out the steps of de-aliasing the at least one aliased angiogram using the ROI mask to create an angiogram of the portion of the subject.

In accordance with yet another aspect of the invention, a method of creating at least one image using a magnetic resonance imaging (MRI) system is disclosed that includes acquiring, with the MRI system and using parallel imaging techniques, a first data set and a second data set of a portion of a subject having a region of interest (ROI) located therein. The method also includes subtracting the first data set and the second data set to generate a difference data set, reconstructing the difference data set into at least one aliased image, and creating a region of interest (ROI) mask from an image of the portion of the subject including the ROI and indicating a masking border surrounding the ROI and substantially excluding tissues surrounding the ROI. The method further includes de-aliasing the at least one aliased image using the ROI mask to create an image of the portion of the subject indicating the ROI and substantially free of surrounding structures.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
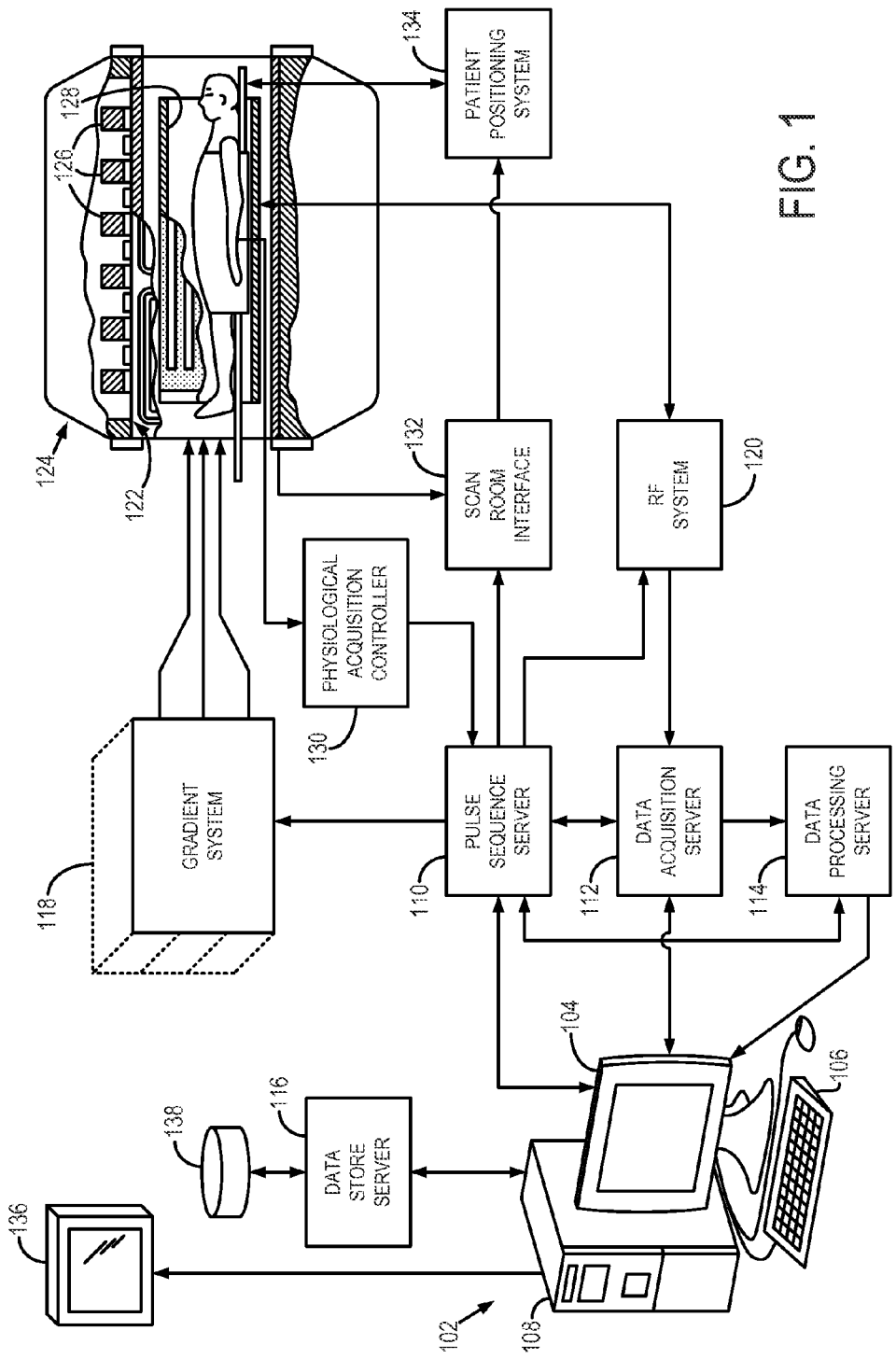
FIG. 1 is a block diagram of an exemplary magnetic resonance imaging ("MRI") system that employs the present invention.

Referring particularly to FIG. 1, an exemplary magnetic resonance imaging ("MRI") system 100 is shown. The MRI system 100 includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114, and a data store server 116. The workstation 102 and each server 110, 112, 114 and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF excitation waveforms are applied to the RF coil 128, or a separate local coil (not shown in FIG. 1), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \quad (1);$$

and the phase of the received MR signal may also be determined:

$$\phi = \tan^{-1}\left(\frac{Q}{I}\right). \quad (2)$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. The data acquisition server 112 may also be employed to process MR signals used to detect the arrival of contrast agent in a magnetic resonance angiography ("MRA") scan. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Figure 2:
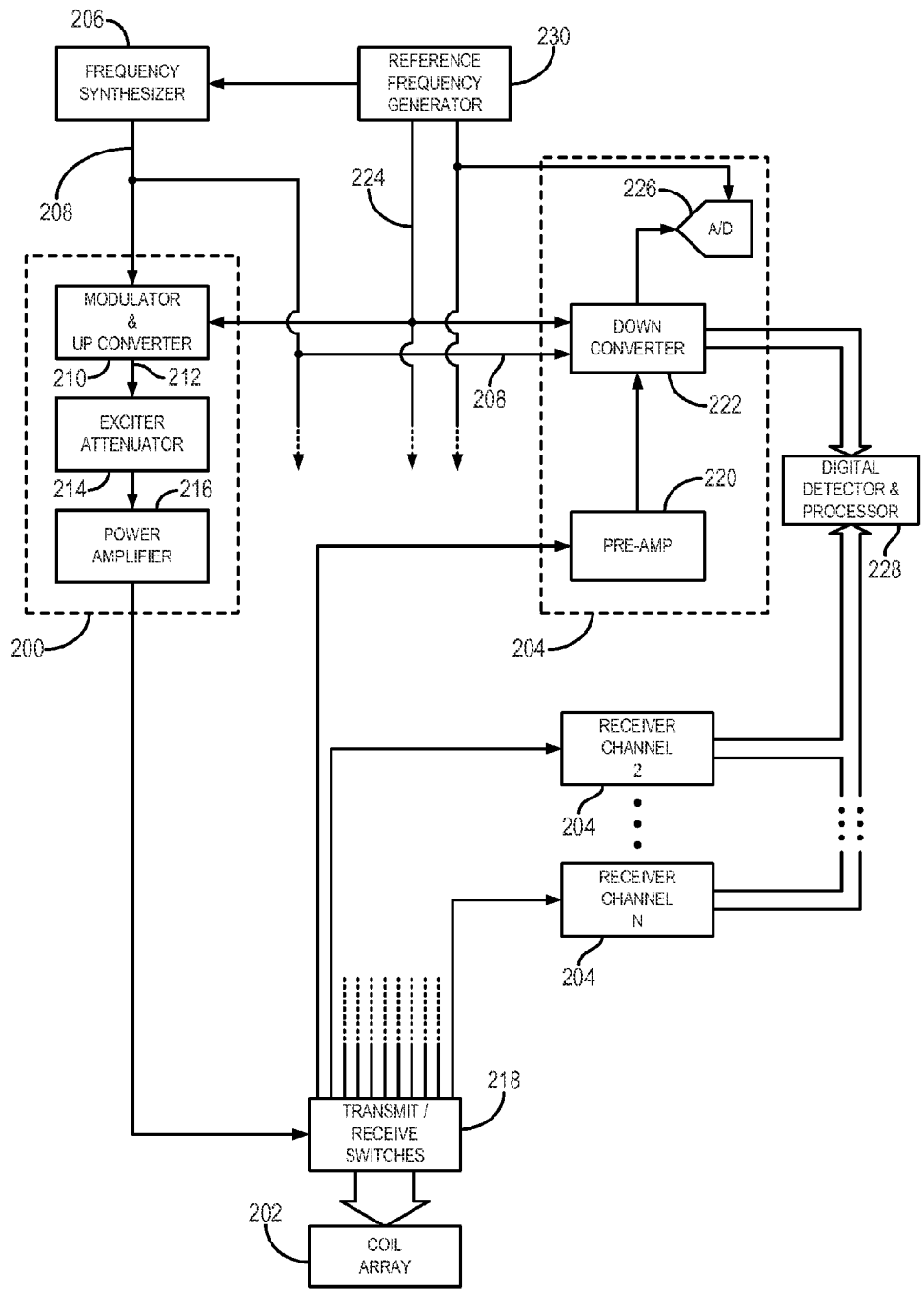
FIG. 2 is a block diagram of an exemplary radio frequency ("RF") system that forms a part of the MRI system of FIG. 1.

As shown in FIG. 1, the radio frequency ("RF") system 120 may be connected to the whole body RF coil 128, or as shown in FIG. 2, a transmitter section of the RF system 120 may connect to at least one transmit channel 200 of a coil array 202, and its receiver section may connect to at least one receiver channel 204 of the coil array 202. Often, the transmitter section is connected to the whole body RF coil 128 or a local transmit coil (not shown), and, in so-called "parallel receiver" coil arrays, each receiver section is connected to a separate receiver channel 204.

Referring particularly to FIG. 2, the RF system 120 includes a transmitter that produces a prescribed RF excitation field. The base, or carrier, frequency of this RF excitation field is produced under control of a frequency synthesizer 206 that receives a set of digital signals from the pulse sequence server 110. These digital signals indicate the frequency and phase of the RF carrier signal produced at an output 208. The RF carrier is applied to a modulator and up converter 210 where its amplitude is modulated in response to a signal, R(t), also received from the pulse sequence server 110. (R(t) here is to be distinguished from the previously defined acceleration factor R.) The signal, R(t), defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 212 is attenuated by an exciter attenuator circuit 214 that receives a digital command from the pulse sequence server 110. The attenuated RF excitation pulses are applied to a power amplifier 216, which drives the RF coil array 202 through a transmit/receive ("T/R") switch 218.

Referring still to FIG. 2, the signal produced by the subject is picked up by the coil array 202 and applied to the inputs of a set of receiver channels 204. A pre-amplifier 220 in each receiver channel 204 amplifies the signal by an amount determined by a digital attenuation signal received from the pulse sequence server 110. The received signal is at or around the Larmor frequency, and this high frequency signal is down-converted in a two step process by a down converter 222, which first mixes the detected signal with the carrier signal on line 208 and then mixes the resulting difference signal with a reference signal on line 224. The down converted MR signal is applied to the input of an analog-to-digital ("ND") converter 226 that samples and digitizes the analog signal and applies it to a digital detector and signal processor 228 that produces 16-bit in-phase (I) values and 16-bit quadrature (Q) values corresponding to the received signal. The resulting stream of digitized I and Q values of the received signal are output to the data acquisition server 112. The reference signal, as well as the sampling signal applied to the ND converter 226, are produced by a reference frequency generator 230.

Using systems such as described above, the present invention allows substantially more voxels to be masked from the SENSE reconstruction, specifically those that are within the object but known to not lie within the vascular structures of interest, than is possible with traditional SENSE CE-MRA techniques employing masks. As such, the present invention provides improved performance because it substantially reduces the overall imaging process without extending the duration of the imaging acquisition or sacrificing the clinical utility of the resulting images due to low SNR or high levels of aliasing.

Current implementations of SENSE-accelerated MR imaging utilizing masking techniques are limited to 1D and 2D SENSE. For 3DFT imaging of the abdomen, and for an FOV which is sized and placed comfortably around the volume of interest (although the abdomen substantially fills the FOV), the percentage of voxels contained in the air outside the abdomen can still be as high as 20 to 30%. For other anatomic regions such as the calves and feet, the percentage of voxels in the air is larger. The present invention exploits these recognitions to overcome challenges of prior-art imaging techniques and facilitates the extension of SENSE-accelerated MR imaging to 3DFT imaging applications.

Figure 3:
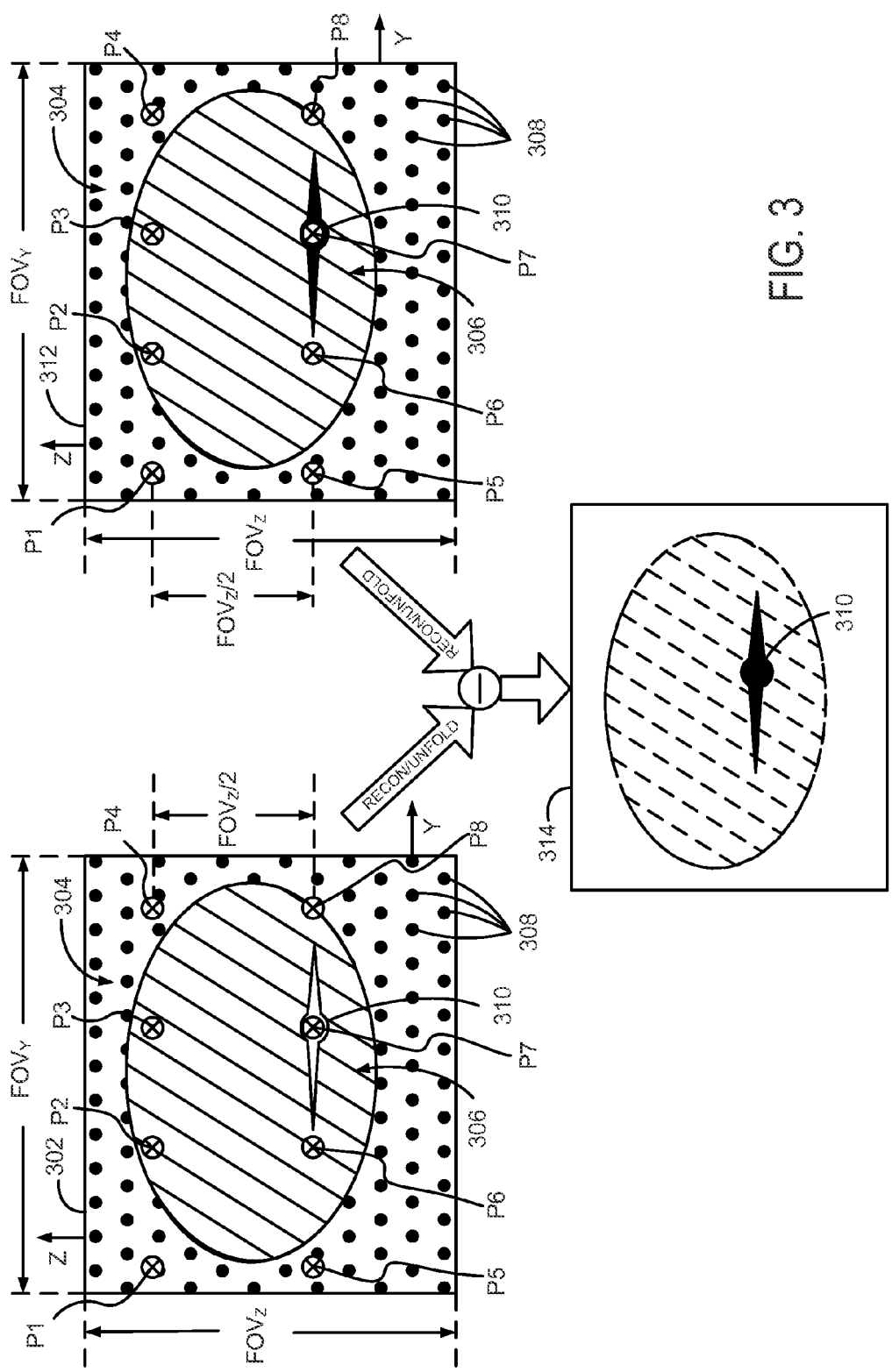
FIG. 3 is a schematic diagram illustrating a prior-art method for performing a contrast enhanced magnetic resonance angiography (CE-MRA), parallel-imaging process using traditional masking techniques.

Specifically, referring to FIG. 3, a schematic diagram is provided that depicts a difference angiography using traditional masking techniques with SENSE reconstruction. A non-contrast image data set 302 is acquired that covers an FOV that extends to create an axial, cross-sectional, slice 304 through an abdomen of an imaging subject 306. As illustrated, the abdomen of an imaging subject 306 only fills a portion of the slice 304 and, thus, the area that surrounds the abdomen of an imaging subject 306 is filled with atmospheric air 308. For simplicity, the abdomen of the imaging subject 306 is shown schematically as an ellipse. Located centrally within the abdomen of the imaging subject 306 is a region of interest (ROI), in this case, a vascular structure 310. The vascular structure 310 is illustrated as a circular cross section of the aorta at the level of the origins of the left and right renal arteries, are illustrated as extending laterally therefrom. As the vascular structure 310 was imaged during the acquisition of the non-contrast image data set 302 without the presence of a contrast agent, the vascular structure 310 is illustrated as having a negative contrast.

Following injection of a contrast agent to the subject, a second, contrast-enhanced image data set 312 is acquired. As illustrated, contrast-enhanced blood is contained in the aorta, and the magnetization in the aorta is substantially higher when compared to that of the non-contrast enhance slice 304 because of the T1 relaxation time of blood has been reduced due to the presence of the contrast agent. As the cross-sectional slice 304 and structures within the slice 304 are, preferably, unchanged during acquisition of the contrast-enhance image data set 312, the components reflected therein are illustrated as being identical, with the noted exception that the contrast associated with the vascular structure 310 is now positive.

For the acquisition of both image data sets 302, 312, the directions Y and Z are identified, which thereby define respective fields-of-view, $FOV_Y$ and $FOV_Z$, along those directions. In the case of a three-dimensional Cartesian MR acquisition, then often the transverse directions shown, Y and Z, are taken as the phase encode directions. In this case, the increment between samples along the $k_Y$ direction of k-space is $1/FOV_Y$ and the increment along $k_Z$ is $1/FOV_Z$. The frequency encode direction, referred to as X, is perpendicular to the Y-Z plane.

With SENSE acceleration, the spacing between samples is increased along both phase encoding directions of k-space, $k_Y$ and $k_Z$ in this example. Because of the reciprocal relationship between k-space sampling increment and FOV described above, the increase in $k_Y$ and $k_Z$ sampling increments causes the $FOV_Y$ and $FOV_Z$ to decrease proportionately.

A consequence of the reduced FOVs being smaller than the size of the subject 306 is that the MR signals at distinct points P1-P8 are now superimposed on each other in the detected signal. Although only one set of eight points is shown, there are many eight-point sets, and all points in the FOV are a member of one such set. This superposition is often referred to as "aliasing." Aliasing results in an image that is generally uninterpretable by the observer. However, with SENSE, the reduced-FOV aliased images are detected from multiple receiver coils, and this information allows the aliased images to be "unfolded" so as to resemble those acquired using normal $FOV_Y$ and $FOV_Z$ values.

Assume, for example, that the SENSE acceleration along the Y direction is $R_Y$=4. This causes a four-fold reduction of $FOV_Y$ in the raw, aliased data and resulting images. Similarly, also assume the SENSE acceleration along the Z direction is $R_Z$=2, causing a two-fold reduction of $FOV_Z$ in the raw data and images. The overall 2D SENSE acceleration, R, is the product of individual acceleration along Y and Z: $R=R_Y \times R_Z=4\times 2=8$. The raw, aliased data and images in this case are a combination of four-fold aliasing along Y and two-fold aliasing along Z.

Aliasing or superposition means that the detected signal is the combination of MR signals originating from distinct points in the object, for exemplary purposes, points P1-P8 are illustrated. For a field-of-view of $FOV_Y/4$, the superimposed points P1-P4, P5-P8 are separated from each other by exactly a distance $FOV_Y/4$ along the Y direction. Similarly, if the field-of-view is additionally reduced to $FOV_Z/2$ along Z, points (P1, P5; P2, P6; P3, P7; and P4, P8) separated by exactly this distance will be superimposed. When these two accelerations are used simultaneously, as assumed in FIG. 3, then the signal formed in each raw, aliased image, is the superposition of the MR signals from eight different points P1-P8 in the original, full, two-dimensional FOV, with the spacing between points obeying the above relationships. Stated another way, in the aliased image formed using the detected signals from each element of the receiver coil array, the signal in the aliased image is the superposition of the true MR magnetization at a set of the eight points P1-P8 in the object. As such, it is difficult to determine the actual magnetization at any one point, such as at point P7 within the aorta.

The superposition of the magnetizations at the set of points P1-P8 in the aliased image and the manner by which they can be individually determined can be explained mathematically. For SENSE unfolding to work, it must be assumed that the MR data sets are detected simultaneously from each of a set of multiple elements of the receiver coil array. Consider an individual, "first," element of such an array that detects MR signals from an object, such as the vascular structure 310 within the subject 306. Depending upon the size and placement of the vascular structure 310 relative to the subject 306, the element will have different sensitivities to the eight points P1-P8. For example, the sensitivity to point P1 might be $S_{11}$, to point P2 might be $S_{12}$, and so on, up to $S_{18}$ for point P8, where the first subscript on S indicates the coil element number and the second subscript indicates the point in the object. The data obtained from that first element during the accelerated MR acquisition are used to form an aliased image. Let A1 be the reconstructed signal in that aliased image using that first coil element corresponding to the superposition of the eight points P1-P8. This can be expressed mathematically as:

$$A1=S_{11}P1+S_{12}P2+S_{13}P3+S_{14}P4+S_{15}P5+S_{16}P6+S_{17}P7+S_{18}P8 \quad (3).$$

Next, consider a second coil element in the receiver coil array. In general, the placement of the second coil element will differ from that of the first element, and thus its sensitivities to the eight points P1-P8 will be different from those for the first element. Let these sensitivities be $S_{21}, S_{22}, \ldots,$ $S_{28}$. In this case, the reconstructed, aliased signal A2 from this second element in the aliased image will be:

$$A2 = S_{21}P1 + S_{22}P2 + S_{23}P3 + S_{24}P4 + S_{25}P5 + S_{26}P6 + S_{27}P7 + S_{28}P8 \quad (4).$$

The above process continues for all elements in the receiver coil array, with each element having an associated, unique sensitivity or "S" values and; thus, creating an equation similar to Eqs. 3-4, but unique to that element.

In SENSE unfolding, the signals in the aliased images from the multiple coil elements are used to restore the unaliased magnetization values at the points of interest. For an overall acceleration R, there must in general be $N_C$ coil elements, where $N_C$ is an integer larger than R. In the above example, it was assumed that R=8, and thus with eight coil elements there would be eight equations similar to Eqs. 3 and 4. From the eight aliased values A1-A8 and assuming that the coil sensitivity values (64 of them in this example) have been previously measured, this results in eight equations for the eight unknowns, P1-P8. This system of equations can be solved mathematically using well-known methods.

It is known that masking can improve SENSE processing. Traditionally, masking has been defined as the process by which points within the field of view are identified that are known to have negligible magnetization. This can generally be done by using images of the object that are acquired to determine the coil sensitivity information. Applying edge detection, a signal threshold, or some alternative process, the overall object of interest can be isolated and the air outside 308 the subject 306 can be masked away and excluded from subsequent consideration because the air 308 has negligible magnetization when compared to the subject 306.

In FIG. 3, in both the non-contrast and contrast enhanced images data sets 302, 312 and consistent with standard SENSE reconstruction techniques, the NMR signal acquired from the air 308 is utilized in the reconstruction process and reflected in the illustrated images. However, because there is no magnetization in the air 308, the reconstructed signal levels are composed exclusively of noise and contribute unfavorably to the image by, for example, potentially obscuring clinically relevant information about the vascular structure 310. However, points P1, P4, and P5 are located in the air 308 outside the subject 306. The masking process, if done effectively, can identify these points P1, P4, and P5, and remove or "mask" them from SENSE processing.

The value of masking can be seen mathematically by considering Eqs. 3 and 4. Using the above example, assume that points P1, P4, and P5 have been identified as having negligible magnetization. The values associated with points P1, P4, and P5 can be forced to be zero in Eqs. 3 and 4 by masking. When this is done, these terms can be eliminated from these equations, leaving simplified forms of equations 3 and 4 as follows $$A1 = S_{12}P2 + S_{13}P3 + S_{16}P6 + S_{17}P7 + S_{18}P8 \quad (5a);$$

$$A2 = S_{22}P2 + S_{23}P3 + S_{26}P6 + S_{27}P7 + S_{28}P8 \quad (5b);$$

and similar equations for A3-A8 all with the terms for P1, P4, and P5 removed. There are still eight equations, as provided by the eight coil elements, but now only five unknowns that must be solved. In general, this results in a more precise solution than the case in which the same eight measurements are used to solve for eight unknowns. Forcing the magnetization at points P1, P4, and P5 to be zero has, in effect, prevented the true magnetization at the other points from being artifactually assigned and shared with points in the air. As illustrated in FIG. 3, the non-contrast enhanced image data set 302 and contrast-enhanced image data set 312 can be reconstructed, unfolded, and then subtracted to yield a difference image/angiogram image 314 where the vascular object 310 is highly distinguished within the image.

Figure 4:
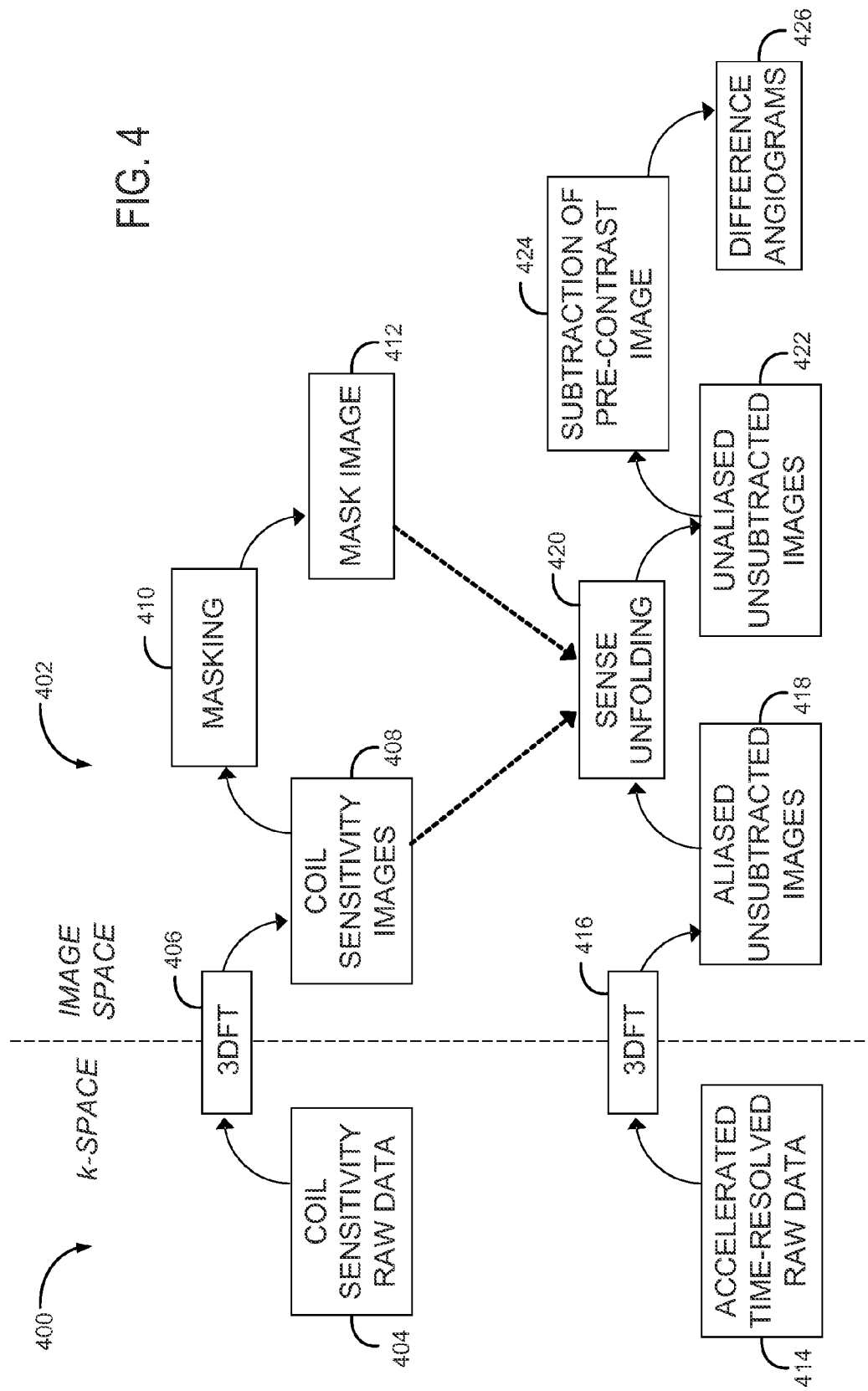
FIG. 4 is a flow diagram corresponding to the schematic diagram of FIG. 3.

FIG. 3, for illustrative purposes, does not reflect the overall process flow performed to carry out such operations. Referring to FIG. 4, a process flow diagram is provided that sets forth the steps typically performed to carry out the process described with respect to FIG. 3 and differentiates steps performed in k-space 400 from those performed in the image domain 402.

Specifically, coil sensitivity data, "raw data" is acquired at block 404 and, as represented by block 406, transformed from k-space/frequency domain 400 to image space 402 using a Fourier transform, such as a 3DFT. The result is a set of coil sensitivity images, represented by block 408. As described above, the coil sensitivity images can be used to perform the above-described masking process at process block 410 to, thereby, create a mask image at block 412.

After acquisition of the coil sensitivity data at block 404, raw accelerated time-resolved data is acquired at block 414 and is transformed, for example, by way of a 3DFT at process block 416 into the image domain 402 as aliased, unsubtracted images at process block 418.

The coil sensitivity images of block 408, also referred to as calibration images, are used to determine coil sensitivity profiles or maps that are used in the SENSE image reconstruction process. Thus, as illustrated, the coil sensitivity images of block 408 are used, along with the mask image of block 412, in a SENSE unfolding process at block 420. The result of the SENSE unfolding process at block 420 are sets of unaliased, but unsubtracted, images represented at process block 422. These unaliased, unsubtracted, images are subtracted against a corresponding pre-contrast image at block 424 to yield difference angiograms at block 426.

Figure 5:
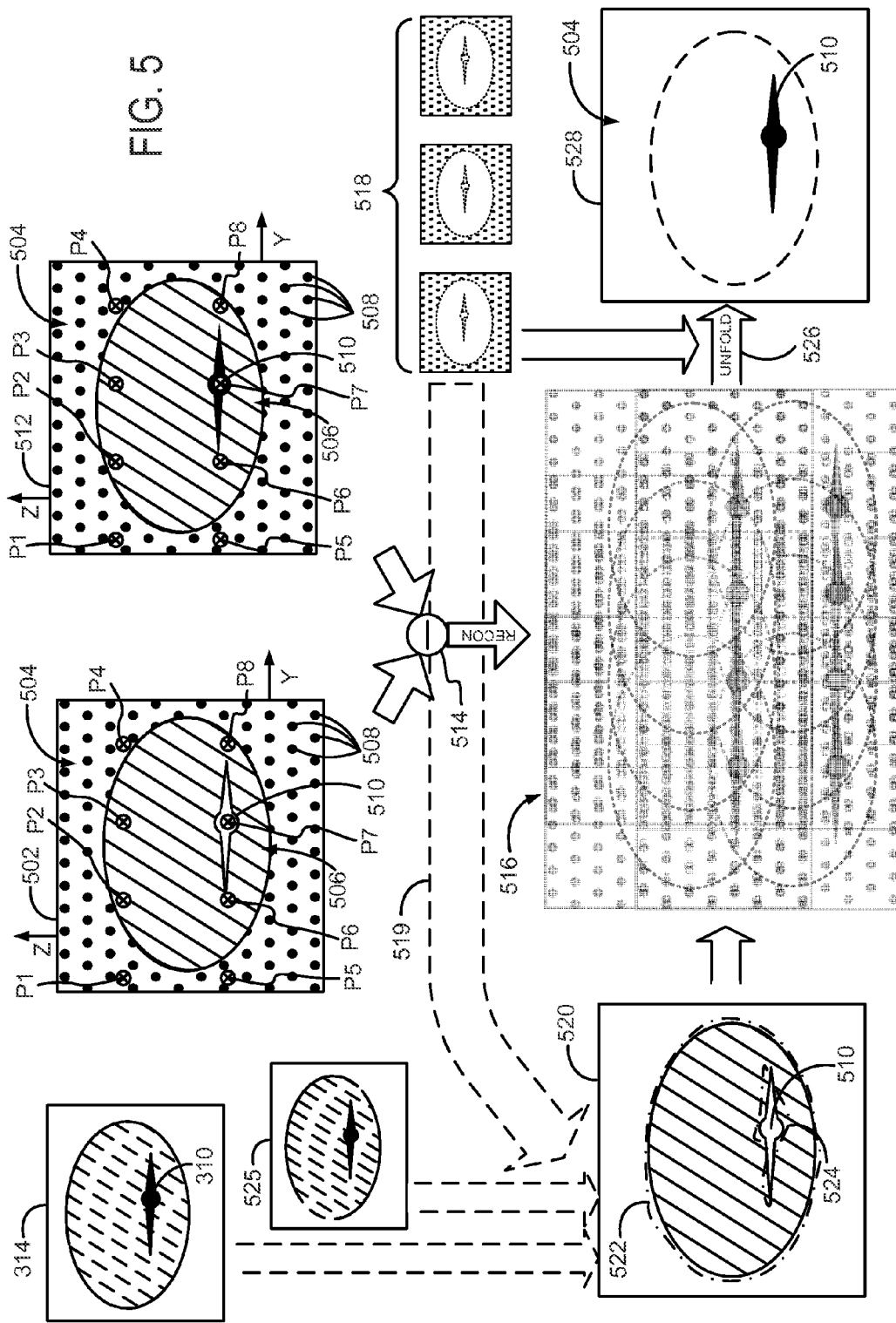
FIG. 5 is a schematic diagram illustrating a method for performing a contrast enhanced magnetic resonance angiography (CE-MRA), parallel-imaging process in accordance with the present invention.

Referring now to FIG. 5, a process for pre-reconstruction, region-of-interest (ROI) isolating, difference imaging in accordance with the present invention will be described. As described above, a non-contrast image data set 502 is acquired. As illustrated, the non-contrast enhanced image data set 502 covers an FOV that extends to create an axial, cross-sectional, slice 504 through an abdomen of an imaging subject 506. As illustrated, the abdomen of an imaging subject 506 only fills a portion of the FOV from which the non-contrast enhanced image data set 502 is acquired and, thus, the area that surrounds the abdomen of an imaging subject 506 is filled with atmospheric air 508. Located centrally within the abdomen of the imaging subject 506 is an ROI, in the illustrated case, a vascular structure 510. Again, the vascular structure 510 is illustrated as circular cross section of the aorta at the level of the origins of the left and right renal arteries which extend laterally. As the vascular structure 510 was imaged without the presence of a contrast agent in image data set 502, the vascular structure 510 is illustrated as having a negative contrast.

Following injection of a contrast agent to the subject, a second, contrast-enhanced image data set 512 is acquired that is substantially similar to that of the non-contrast enhanced image data set 502, with the noted exception that the contrast associated with the vascular structure 510 is now positive.

In both the non-contrast and contrast enhanced image data sets 502, 512, the NMR signal acquired from the air 508 constitutes a substantial portion of the signals acquired, as the air 508 fills approximately 50 percent of the FOV. However, because there is no magnetization in the air 508, the signal levels are composed exclusively of noise and contribute unfavorably to the image by, for example, potentially obscuring clinically relevant information about the vascular structure 510. As described above, this situation can be handled using a traditional mask to remove signals associated with the air 508.

In traditional masking techniques, such as described, above, the subject border 518 is used to mask unsubtracted, but reconstructed (and, thus, aliased) images that are then unfolded. Only once reconstructed, masked and unfolded are the pre- and post-contrast images subtracted. However, in accordance with the present invention, the contrast-enhanced image data set 512 and the non-contrast enhanced image data set 502 may be subtracted 514, even before transformation into the image domain. That is, the raw, pre- and post-contrast image data sets may be subtracted and then transformed to the image domain. As such, a set of subtracted, aliased angiograms 516 are yielded.

To overcome the drawbacks presented by unfavorable contributions to the images by signals from the air 508 and to reduce the processing time, as described, masking can be used to remove signal from the air 508. As mentioned, using conventional SENSE imaging processes, low-resolution, calibration images 518 are available to the clinician. As is commonly employed with most parallel imaging techniques, a set of calibration images 518, one image per coil element, is acquired to determine coil sensitivity profiles or maps that are used in the SENSE image unfold process. Also, these calibration images 518 can be reconstructed and, as described above and represented by arrow 519, utilized to create a mask image 520. The mask image 520 may include an estimate of a border 522 of the abdomen of the imaging subject 506. However, in accordance with the present invention, an alternative (or even additional) border 524 can be designated about a particular region of interest (ROI), in the illustrated case, the vascular structure 510, within the abdomen of the imaging subject 506.

It is contemplated that the masking process of the present invention may be achieved based on one or more of a variety of data sources. Rather than perform the SENSE reconstruction and unfolding directly on the unsubtracted data, as described above, one variation is to first perform the standard SENSE reconstruction using current masking techniques to yield a traditional difference angiogram 314, such as described with respect to FIG. 3. From this traditional image 314, the vascular structures 510 can be identified using, for example, a thresholding operation designed to eliminate all voxels with signals that are below a specific threshold. The SENSE unfolding is again performed with a ROI mask 524 based on the thresholding.

Another variation of the above is to reconstruct the full time series with standard reconstruction, and require that a voxel to be identified as corresponding to the ROI/vessel if its time-varying behavior meets a given condition, such as a thresholding. Within this time-varying context, the thresholding condition may be required to extend over a desired image frames as another or secondary condition of the thresholding. Voxels that do not meet the condition(s) are then flagged as being non-vascular, and they are masked and removed from further consideration in the SENSE unfolding. Other variations of this are also possible, such as requiring that a vascular voxel have at least one adjacent voxel in any direction that is also identified as being vascular and the like.

In yet another variation, it may be desirable to use a priori images 525, for example, even from prior imaging sessions. In such instances, the coil sensitivity images 510 may be used to register the a priori images 525 with the images 516 of the current acquisition.

Regardless of the specific images or mechanism used for identifying the ROI/vascular object, the result is the creation of masks of the ROI/contrast-enhanced vasculature 520, 524.

As such, signal levels associated with regions outside the ROI border 524 (and, if also selected, outside the abdomen border 522) are forced to be zero or another selected value in the SENSE processing. Specifically, points P1-P8 are again illustrated within data sets 502 and 512 as an example. As described above, the aliased subtraction angiogram 516 will benefit from masking to remove points P1, P4, and P5. However, the present invention provides a mechanism by which the SENSE unfolding can be improved upon by additional masking. Specifically, the preferable, ROI mask 524 can be used and, thereafter, SENSE unfolding can be preformed to yield an unaliased, angiogram with substantial contrast associated with the desired vascular structure 510, and all other signals acquired from within the slice 504 removed or reduced. Specifically, the masks are used along with the coil sensitivity images to perform a SENSE unfolding process 526 on the aliased subtraction angiograms 516, which yields unaliased subtraction angiograms 528.

More particularly, continuing with the example provided above, points P1, P4, and P5 were previously identified as being associated with the air 508 and removed using conventional masking. With the present invention, the difference angiogram 516, mask image 520, or other image(s) providing a priori information can be used to identify points associated with the desired vascular structure 510. For example, a signal threshold or similar approach may be used to analyze the aliased difference angiogram 516, the calibration images 518, or other a priori images 314, 525, to identify points within the vascular structure 510. This process can identify point P7 as being squarely within the vascular structure 510, and excludes points P2, P3, P6, and P8, as being outside the vascular structure 510. The resultant equations to be used for unfolding of the aliased difference image then become:

$$A1 = S_{17} P7 \quad (6a);$$

$$A2 = S_{27} P7 \quad (6b).$$

Similar equations follow for A3-A8. SENSE unfolding can now be done with the benefit of many more points being masked away. The ROI-specific masking and pre-reconstruction subtraction of the present invention, thus, markedly reduces the complexity of the mathematical inversion of the eight equations. Specifically, in the context of the present example, the pre-reconstruction subtraction and ROI-specific masking reduces the mathematical inversion to one unknown and further prevents the magnetization in Point P7 from being artifactually shared with any other points in the field of view.

Figure 6:
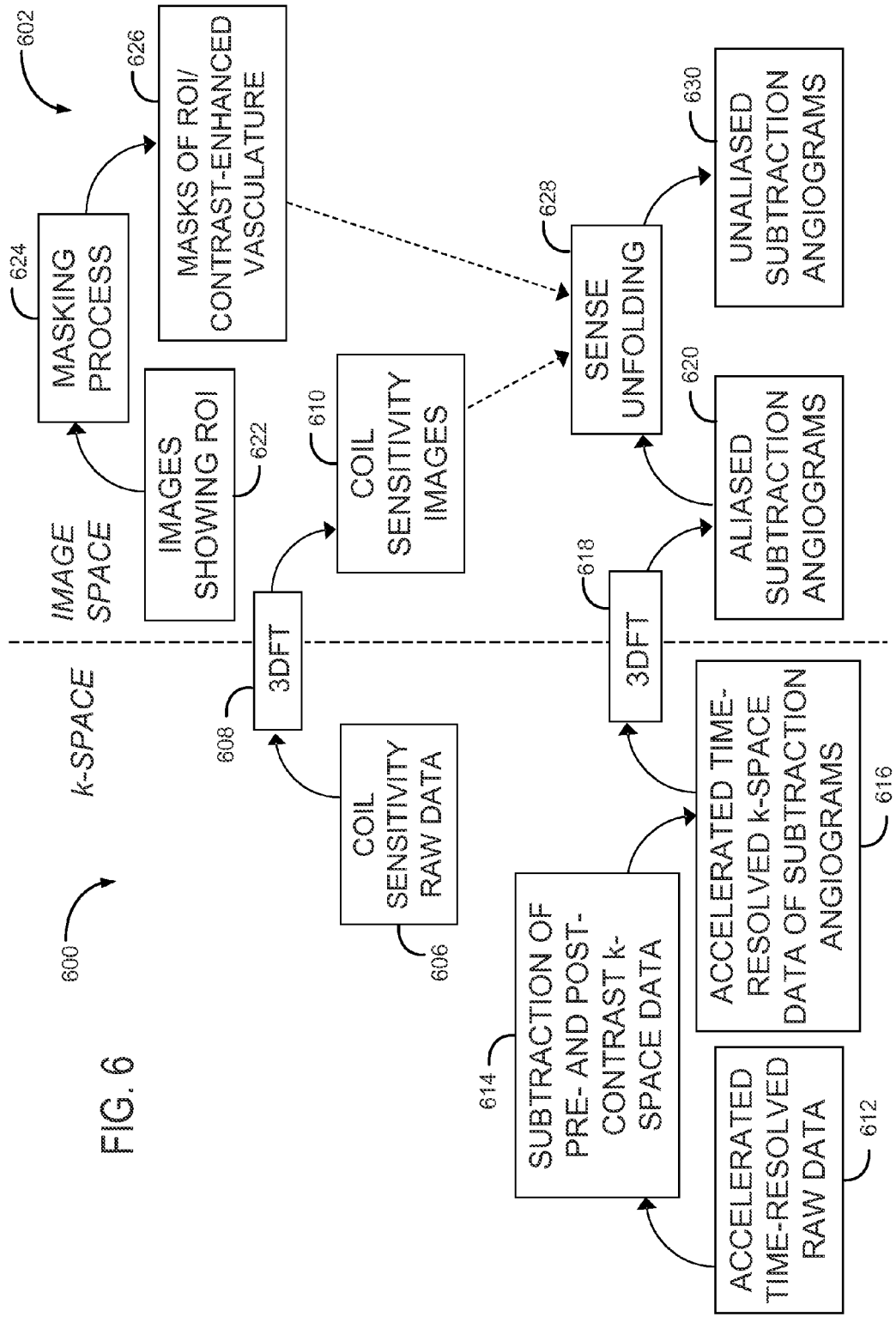
FIG. 6 is flow diagram corresponding to the schematic diagram of FIG. 5.

The present invention can also be illustrated with reference to a flow diagram, rather than illustrated schematically, as in FIG. 5. Referring to FIG. 6, a process flow diagram is provided that sets forth the steps typically performed to carry out the process in accordance with the present invention and differentiates steps performed in k-space 600 from those performed in the image domain 602.

As described above, coil sensitivity "raw data" is acquired at block 606 and, as represented by block 608, transformed from k-space/frequency domain 600 to image space 602 using a Fourier transform, such as a 3DFT. The result are coil sensitivity images, represented by block 610.

Once non-contrast enhanced data has been acquired, including coil sensitivity data, accelerated time-resolved data is acquired, as represented by block 612. As described above, unlike traditional SENSE-based angiography techniques, the acquired pre- and post-contrast enhanced data are subtracted as "raw," k-space data, as indicated at block 614. As such, at block 616, a set of accelerated time-resolved k-space data for the desired subtraction angiograms is created, which is then transformed, for example, by way of a 3DFT at block 618 to yield a set of aliased subtraction angiograms at block 620, which corresponds to the subtracted, aliased angiograms 516 of FIG. 5.

Thus, the present invention provides a system and method whereby the reconstruction is performed using difference data, resulting in voxels where the signal is appreciable only in those voxels in which contrast enhancement occurs. As described above, the coil sensitivity images or other images such as subtraction angiograms made using standard masking, may be used as the images showing the ROI at block 622.

Regardless of the specific images or mechanism used for identifying the ROI/vascular object, the result is the creation of masks of the ROI/contrast-enhanced vasculature 626. The masks are used along with the coil sensitivity images to perform a SENSE unfolding process on the aliased subtraction angiograms at block 628, which yields unaliased subtraction angiograms at block 630.

Using the present invention, the unaliased subtraction angiograms are yielded with increased signal-to-noise (SNR) because undesired signals from air and even background tissue surrounding the ROI/vascular object are reduced or removed by the masking process. Furthermore, the above-described process, in at least some instances, is less computationally burdensome because the signals subjected to the computationally-burdensome SENSE unfolding process are limited by the mask to those corresponding to the ROI/vascular object, rather than including all surrounding tissues.

A method has been described for providing improved performance of SENSE reconstruction in contrast-enhanced MR angiography. The method is based on noting that in CE-MRA difference images, as opposed to unsubtracted MR images, the voxels that have non-zero signal can be advantageously limited to the vascular system. This allows the masking process to identify more voxels in the SENSE unfolding process that are known to have zero signal and that can then be defined to have such during unfolding. This then reduces the level of artifactual dispersion of true signal into non-vascular voxels from the voxels within the vasculature, preserving SNR.

The present invention has been described in terms of one or more preferred embodiments, and it should be appreciated that many equivalents, alternatives, variations, and modifications, aside from those expressly stated, are possible and within the scope of the invention.

The invention claimed is:

1. A method of creating at least one angiographic image using a magnetic resonance imaging (MRI) system, the method comprising:
   acquiring, with the MRI system and using parallel imaging techniques, a pre-contrast image data set and a post-contrast image data set of a portion of a subject having a vascular structure extending therethrough;
   subtracting the pre-contrast image data set and the post-contrast image data set to generate a difference angiogram data set;
   reconstructing the difference angiogram data set into at least one aliased angiogram;
   creating a region of interest (ROI) mask from an image of the portion of the subject including the vascular structure and indicating a masking border surrounding the vascular structure and substantially excluding tissues surrounding the vascular structure; and
   de-aliasing the at least one aliased angiogram using the ROI mask to create an angiogram of the portion of the subject.

2. The method of claim 1 wherein creating the ROI mask includes analyzing the image of the portion of the subject including the vascular structure using a thresholding criteria to identify the vascular structure and borders of the vascular structure and wherein the masking border follows the borders of the vascular structure.

3. The method of claim 1 wherein de-aliasing the at least one aliased angiogram using the ROI mask includes setting signals associated with points outside the masking border to zero.

4. The method of claim 1 wherein the parallel imaging techniques includes a sensitivity encoding (SENSE) parallel imaging process and de-aliasing includes performing unfolding process.

5. The method of claim 1 wherein the image of the portion of the subject is an a priori image of the subject.

6. The method of claim 1 further comprising de-aliasing the at least one aliased angiogram to generate the image of the portion of the subject, creating the ROI mask from the image of the portion of the subject, and then de-aliasing the at least one aliased angiogram using the ROI mask to create the angiogram of the portion of the subject.

7. The method of claim 1 wherein the pre-contrast image data set and the post-contrast image data set are three-dimensional (3D) data sets.

8. A magnetic resonance imaging (MRI) system comprising:
   a magnet system configured to generate a polarizing magnetic field about at least a portion of a subject arranged in the MRI system;
   a plurality of gradient coils configured to apply a gradient field to the polarizing magnetic field;
   a radio frequency (RF) system configured to apply an excitation field to the subject and acquire MR image data therefrom in parallel from a plurality of channels;
   a computer system programmed to at least carry out the steps of:
      acquiring a pre-contrast image data set and a post-contrast image data set of a portion of a subject having a vascular structure extending therethrough;
      subtracting the pre-contrast image data set and the post-contrast image data set to generate a difference angiogram data set;
      reconstructing the difference angiogram data set into at least one aliased angiogram;
      creating a region of interest (ROI) mask indicating a masking border surrounding the vascular structure and substantially excluding tissues surrounding the vascular structure; and
      de-aliasing the at least one aliased angiogram using the ROI mask to create an angiogram of the portion of the subject.

9. The system of claim 8 wherein creating the ROI mask includes analyzing an a priori image of the portion of the subject including the vascular structure using a thresholding criteria to identify the vascular structure and contour the masking border based on borders of the vascular structure.

10. The system of claim 9 wherein the a priori image of the portion of the subject is acquired from a coil sensitivity image.

11. The system of claim 9 wherein the computer system is further programmed to carry out the step of de-aliasing the at least one aliased angiogram to generate the a priori image of the portion of the subject and carry out the step of de-aliasing the at least one aliased angiogram using the ROI mask to create the angiogram of the portion of the subject.

12. The system of claim 8 wherein de-aliasing the at least one aliased angiogram using the ROI mask includes setting signals associated with points outside the masking border to zero.

13. The system of claim 8 wherein the pre-contrast image data set and the post-contrast image data set are three-dimensional (3D) data sets.

14. A method of creating at least one image using a magnetic resonance imaging (MRI) system, the method comprising:
acquiring, with the MRI system and using parallel imaging techniques, a first data set and a second data set of a portion of a subject having a region of interest (ROI) located therein;
subtracting the first data set and the second data set to generate a difference data set;
reconstructing the difference data set into at least one aliased image;
creating a region of interest (ROI) mask from an image of the portion of the subject including the ROI and indicating a masking border surrounding the ROI and substantially excluding tissues surrounding the ROI; and
de-aliasing the at least one aliased image using the ROI mask to create an image of the portion of the subject indicating the ROI and substantially free of surrounding structures.

15. The method of claim 14 wherein creating the ROI mask includes analyzing the image of the portion of the subject including the ROI using a thresholding criteria to identify the ROI and borders of the ROI and wherein the masking border follows the borders of the ROI.

16. The method of claim 14 wherein de-aliasing the at least one aliased image using the ROI mask includes setting signals associated with points outside the masking border to zero.

17. The method of claim 14 wherein the image of the portion of the subject is an a priori image of the subject.

18. The method of claim 14 further comprising de-aliasing the at least one aliased image to generate the image of the portion of the subject, creating the ROI mask from the image of the portion of the subject, and then de-aliasing the at least one aliased image using the ROI mask to create the image of the portion of the subject substantially free of surrounding structures.

19. The method of claim 14 wherein the pre-contrast image data set and the post-contrast image data set are three-dimensional (3D) data sets.

20. The method of claim 14 wherein the parallel imaging techniques includes a sensitivity encoding (SENSE) parallel imaging process and de-aliasing includes performing unfolding process.

* * * * *